(12) United States Patent
Naydenov et al.

(10) Patent No.: US 6,377,843 B1
(45) Date of Patent: Apr. 23, 2002

(54) TRANSTELEPHONIC MONITORING OF MULTI-CHANNEL ECG WAVEFORMS

(75) Inventors: Nartzis Naydenov; Anthony Marchesini, both of Wayne, NJ (US)

(73) Assignee: Paceart Associates, L.P., Fairfield, NJ (US)

( * ) Notice: Subject to any disclaimer, the term of this patent is extended or adjusted under 35 U.S.C. 154(b) by 0 days.

(21) Appl. No.: 09/518,546

(22) Filed: Mar. 3, 2000

(51) Int. Cl.[7] .................................................. A61B 5/04
(52) U.S. Cl. ........................................ 600/509; 128/904
(58) Field of Search ................................ 128/903–904; 600/508–509

(56) References Cited

U.S. PATENT DOCUMENTS 3,886,314 A * 5/1975 Pori
3,898,984 A * 8/1975 Mandel et al.
4,658,831 A * 4/1987 Reinhard et al.
4,938,229 A    7/1990 Bergelson et al.
5,333,617 A * 8/1994 Hafner
5,467,773 A   11/1995 Bergelson et al.
5,735,285 A    4/1998 Albert et al.

* cited by examiner

*Primary Examiner*—Mark Bockelman
(74) *Attorney, Agent, or Firm*—Cooper & Dunham LLP

(57) ABSTRACT

Remote monitoring of biological signals such as ECG waveforms, in which an FM encoded version of an ECG waveform is transmitted from a patient's home to a central station where it is analyzed to estimate local frequencies at many more time points than the zero crossovers of the FM signal. A plurality of ECG waveforms is encoded in a composite FM signal any one point of which can represent at the same time a number of ECG waveforms. The composite waveform is analyzed at the central station to extract and reconstruct the individual waveforms by separation in the frequency domain.

20 Claims, 1 Drawing Sheet

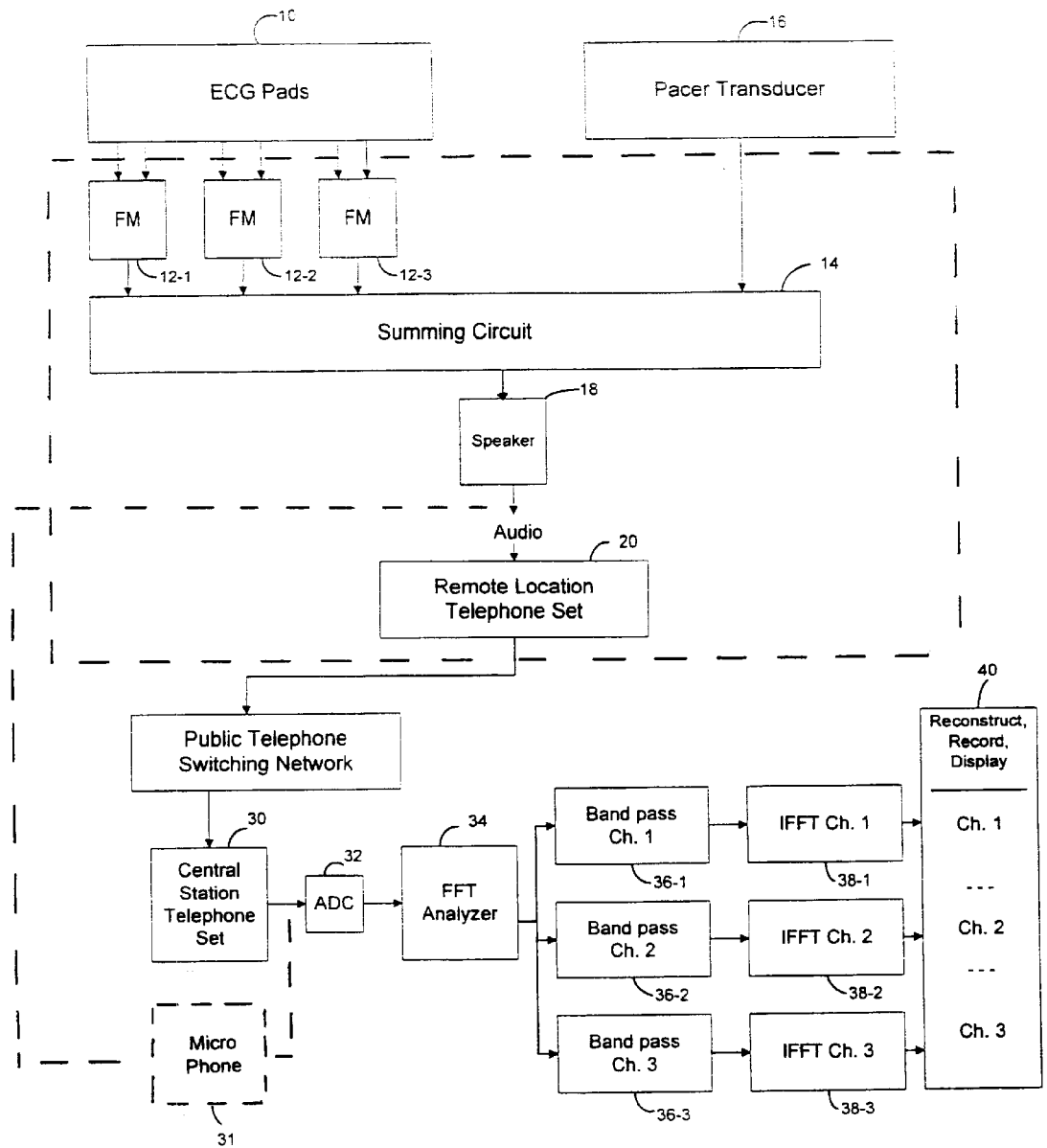

TRANSTELEPHONIC MONITORING OF MULTI-CHANNEL ECG WAVEFORMS

FIELD

This patent specification is in the field of remote monitoring of biomedical data, such as ECG (electrocardiogrupham) data.

BACKGROUND

Transtelephonic monitoring of cardiographic data such as ECG waveforms and heart pacer information has been used for many years. Typically, a cardiac transducer at a patient's home produces an electrical ECG signal in the form of a voltage across a pair of ECG pads that are in electrical contact with the patient's body. The resulting ECG waveform is used to frequency modulate a carrier, and the resulting FM signal drives a speaker producing an acoustic FM signal played into the mouthpiece of a telephone receiver that converts the acoustic signal back to an electrical FM signal. Via the telephone network, a central station receives the transmitted signal and processes it to reconstruct, display, and record the ECG waveform or to extract other information. If the cardiac signal is pacer related, the information of interest could be the duration of a pacer pulse or the time between pulses. The conversion to an acoustic signal and back to an electrical signal can be avoided if the patient has suitable equipment and skill for the purpose. Examples of transtelephonic monitoring of cardiac information can be found in U.S. Pat. Nos. 4,938,229 and 5,467,773 (each incorporated by reference herein), and 5,735,285, as well as in references cited in said patents.

The assignee of this patent specification supplies such equipment and services, described further at its Website. Typically, information from different ECG pads or combinations of pads (vectors), or from a pacer, is embedded in the FM signal serially, and packets of additional information such as device ID and time stamps usually are inserted. Only one ECG waveform, or only one pacer pulse, or only one item of identifying information, modulates the carrier at any one time. It is believed that several years ago an entity called the Cardiac Evaluation Center in Milwaukee, Wis. offered, and may still be offering, a two-channel transmitter and a proprietary receiver, encoding two ECG waveforms at the same time into a single FM signal that is separated at a proprietary receiver believed to have used analog bandpass filters for the separation. It is not known what technique that system used to demodulate the FM signal.

In the two patents incorporated by reference herein, the FM signal was demodulated at the receiving station to extract the ECG waveform by finding the zero crossings of the FM signal and measuring the time between those zero crossings. In particular, the patented systems counted a clock during the intervals between adjacent zero crossings and converted the counts to frequency, thereby reconstructing the original ECG waveform. U.S. Pat. No. 5,735,285 is understood to propose another zero crossing detection technique, involving an examination of the area where digitized samples of the FM signal transition between positive and negative values. While such zero crossing analysis of the FM signal, with appropriate suppression of noise and other sources of inaccuracies, has been used for years, it is believed that a need still remains for: (1) a more accurate and reliable reconstruction of the original ECG waveform; (2) the simultaneous transmission of multiple ECG waveforms or other information coupled with such more accurate and reliable reconstruction of the original information; and (3) such simultaneous transmission demodulated at the receiving station using a general purpose computer that can be conveniently adapted through programming to different formats of information transmission and can be less costly and more acceptable than proprietary hardware.

SUMMARY

This patent specification discloses a system and a method for remotely monitoring, at a central station, cardiac conditions existing at a remote station. In a preferred embodiment, three or more ECG waveforms are derived from a patient at a local station. These ECG waveforms frequency modulate respective different carriers to thereby produce three or more respective FM signals. These FM signals are combined into a composite FM signal containing concurrent information from the three or more ECG waveforms, and are transmitted to a central station. At the central station, the received composite FM signal is processed both in the time domain and in the frequency domain to reconstruct the three or more individual ECG waveforms in a manner that comprises estimating local frequencies at portions of the composite FM signal that are substantially closer to each other than zero crossovers of the composite FM signal. The process calculates local phase differences and uses them to estimate said local frequencies. The local phase differences are calculated by combining digital samples of the composite FM signal with a phase shifted version of the digital samples.

BRIEF DESCRIPTION OF THE DRAWING

The FIGURE illustrates a system embodying a preferred example of the disclosure.

DETAILED DESCRIPTION OF THE PREFERRED EMBODIMENTS

Cardiac ECG Event Monitors, Loop Recorders and Post Event Recorders are examples of sensor/transmitters used at a remote location such as a patient's home. Multi-channel sensor/transmitters produce several channels of ECG waveforms, e.g., from different combinations of ECG pads. One known pattern is to use three ECG waveforms derived from differences between signals from three pairings of ECG pads (three vectors). In a preferred embodiment, the system described herein simultaneously encodes the three ECG waveforms into a single FM signal at the remote location, and reconstructs the ECG waveforms at a receiving station using techniques more reliable than zero crossing detection. In the preferred embodiment, the reconstruction of the ECG waveforms is implemented solely through a general purpose computer, such as a PC, running suitable utility and application programs. While the detailed description below uses the example of three ECG waveforms simultaneously encoded into a single FM signal, in its general form the disclosure herein is applicable to N waveforms, where $N \geq 2$, and to biomedical signals in addition to ECG waveforms. In addition, the techniques disclosed herein for reconstructing a waveform more reliably than when using zero crossing detection are applicable to the case where only a single waveform is encoded in the FM signal.

At the transmitting end (typically the patient's home), the patient uses a sensor/transmitter that is otherwise similar in FM encoding technique to those currently supplied by the assignee hereof but FM encodes each of three ECG waveforms into a respective channel and then sums the three FM encoded channels into a single, composite FM signal. For example, a first ECG channel FM modulates a 1700 Hz carrier in a frequency band of 1500–1900 Hz for a first channel of ECG data, a second ECG channel uses a 1950–2350 Hz band on a 2150 Hz carrier, and a third ECG channel uses a 2400–2800 Hz band on a 2600 Hz carrier. The resulting three FM signals are summed into a composite FM signal that is transmitted to the central station. Additional data such as, without limitation, an ID of the transmitting device, pacemaker pulse measurements, and time stamps, can be embedded in the composite FM signal, such as by the known and long used techniques of shifting frequency for several milliseconds out of a signal band frequency, thus indicating the presence of binary data in the FM analog signal. The transmission can be by first converting the composite FM signal into an acoustic signal by a speaker at the sensor/transmitter and playing the acoustic signal into the receiver of a telephone connected over the public telephone system to the central or receiving station, or a direct electrical transmission can be used that does not go through an audio stage.

At the central station, the composite FM signal received over the telephone line is supplied to a general purpose digital computer such as a PC with a sound card, and is analyzed to extract the information defining the three ECG channels, as well as additional information that may have been encoded therein. In principle, the process carried out at the central station converts the received composite FM signal to digital samples x(t), separates them into frequency bands matching the individual FM signals, finds for each band the difference in instantaneous frequency between adjacent digital samples, and uses these frequency differences to reconstruct the original ECG waveforms and any other data of interest.

Referring to FIG. 1 for an illustration of a system using an embodiment disclosed herein, ECG pads 10 used as known at a remote location such as a patient's home generate three channels or vectors of ECG analog waveforms. A local transmitter 11 comprises FM encoders 12-1, 12-2, and 12-3 each encoding a respective channel of ECD data into a frequency modulated analog waveform in a respective frequency band. Local transmitter 11 also includes a summing device 14 which combines the three FM channels into a single, composite FM signals. If a pacer 16 is used, summing device 14 may embed pacer-related information in the composite FM signal as known in the art. Further as known in the art, summing device 14 may embed in the composite FM signal other information such as an ID of the local transmitter, a time stamp, etc. A speaker 18 at the remote location converts the composite FM signal into an audio signal which a receiver of a remote location telephone 20 converts back to a composite, analog electrical FM signal. This FM signal is transmitted through the public telephone switching system, or through some other communication link, to a central station for analysis and recording. If special equipment and skills are available at the remote location, the conversion to an audio signal and back to an analog electrical signal can be avoided, and the composite FM signal from summing device 14 can be transmitted directly to the central station using a suitable communication link.

At the central location, a telephone unit 30 receives the composite FM signals and supplies it to a suitably programmed general purpose computer such as PC with a sound card. Using the sound card as an ADC (analog-to-digital converter) 32, the central station converts the received composite FM signal to arrays of time domain digital samples x(t), which an FFT (Fast Fourier Transform) analyzer 34 converts to arrays of frequency domain digital samples fft(t). These samples fft(t) are separated into three bands, corresponding to the three channels of ECG information, at bandpass filters 36-1, 36-2, and 36-3, and the output of each bandpass filter is subjected to IFFT (Inverse Fast Fourier Transform) analysis at a respective one of analyzers 38-1, 38-2, and 38-3. A unit 40 receives the output of these analyzers and reconstructs, records and displays the three ECG waveforms. If additional information, such as pacer information is embedded in the composite FM signals, a pacer analyzer 42 extracts it and supplies it to unit 40 for display and recording. The equipment at the central station can be, and in a preferred embodiment is, implemented by programming a PC. As earlier noted, conventional PC sound card hardware and utilities of a PC are used to digitize the composite FM signal. FFT analyzer 34 can be implemented by using an off-the-shelf FFT program. Bandpass filters 36 can be implemented by nulling certain frequency bins as discussed below. IFFT analyzers 38 can be implemented by using off-the-shelf IFFT and Hilbert transform programs. Pacer analyzer 42 can be implemented as known in the art and used by the assignee hereof for years for single channel ECG data. Finally, unit 40 can be implemented using the conventional data storage and display capacities of a PC.

In an alternative embodiment, the path starting with remote location telephone set 20 and ending with central station telephone set 30 can be replaced by a microphone 31 that is sufficiently close to speaker 18 to convert the sound from speaker 18 into an analog electrical signal, which analog signal is then supplied to ADC 32. As a further alternative (not illustrated in the drawing), the analog electrical signal from summing circuit 14 can be supplied directly to ADC 32, thereby eliminating the path starting with speaker 18 and ending with central station telephone set 30.

In an exemplary and non-limiting example disclosed herein, the process as applied to ECG vectors includes the following main steps that are computer-implemented using a PC with a sound card and suitable programming:

1. At the patient's home, or another remote or transmitting location, obtain three ECG channels (vectors), each in the form of a respective ECG electrical waveform. This can be done using currently commercially available equipment, for example equipment available from the assignee hereon;
2. Use each ECG vector to frequency modulate a respective carrier to thereby generate three FM ECG signals, each in a respective frequency band, e.g. a carrier frequency of 1700 Hz and bandwidth of 1500–1900 Hz for channel 1, a carrier frequency of 2150 Hz and bandwidth of 1950–2350 Hz for channel 2, and a carrier frequency of 2600 Hz and bandwidth of 2400–2800 Hz for channel 3. The encoding for each individual channel can also be done using equipment currently available commercially, for example from the assignee hereof;
3. Sum the three FM ECG signals into a single, composite FM signal. This can be done using an analog summing circuit, for example currently commercially available circuits of this type;
4. Convert the composite FM signals into an audio signal. This can be done using a speaker, such as in currently commercially available home transmitter, such as those available from the assignee hereof;
5. Convert the audio signal back to a composite FM signal and transmit as such to a central station. This can be done using a telephone set at the patient's home, such as described in the patents incorporated by reference herein;

6. Digitize the composite FM signal received at the central station into arrays of time domain digital samples x(t). This can be done using the sound card of a conventional PC. The preferred format is to digitize the incoming composite FM signals at sampling rate of 8 Khz (8,000 samples per second), into arrays of 1024 samples each, overlapped by 512 samples, i.e., the first 512 samples of the second array are the same as the last 512 samples of the first array, etc. Each sample is 16 bits long, representing the instantaneous amplitude (x) of the composite FM signal at a respective time (t). The result is a succession of arrays of 1024, 16-bit values each, overlapped by 512 samples. For computational convenience in a preferred embodiment, the arrays are converted to single precision arrays:

7. Filter the digital samples x(t) to reduce noise, e.g., with a Hamming Window filter. This can be done using an off-the-shelf utility for Hamming Window filtering in a PC;

8. Pass the arrays of digital samples x(t) through an FFT (Fast Fourier Transform) Analyzer to convert them into frequency domain digital sample arrays fft(t), where each sample is a value of a coefficients of a Fourier series representation of the x(t) arrays. This can be done using an off-the-shelf FFT program running in a PC. The result is the conversion of each of the 1024-element x(t) array into a corresponding 1025-element, complex-conjugate symmetric fft(t) array. The elements of the fft(t) array are related to the values of coefficients for respective frequencies, and are stored in respective frequency bins in PC memory. Additional filtering can be done at this point to null coefficient values for frequencies outside the bandwidths of the three ECG signals. For example, a bandpass filter of 750–3250 Hz can be applied by zeroing frequency bins corresponding to 0 Hz, 7.8125 Hz, 15.625 Hz, . . . , 742.1875 Hz (i.e., elements 1–95 inclusive of each fft(t) array), and bins corresponding to 3257.8125 Hz, 3265.625 Hz, . . . 4000 Hz (i.e., elements 417–513 of each fft(t) array);

9. Separate the samples fft(t) into respective spectral bands each matching the frequency band of a respective one of the ECG channels that were FM encoded at the remote location (the patient's home). This can be done by making three copies of the (filtered) fft(t) array and in each nulling the elements that correspond to frequencies outside the frequency band of the respective ECG signal;

10. Pass the samples fft(t) through IFFT (Inverse Fast Fourier Transform) and Hilbert transform analysis to obtain arrays of digital samples of an analytical signal z(t), where each z(t) sample has a real part matching the time domain samples x(t) of the composite FM signal and an imaginary part jh(t) that matches a Hilbert transform of x(t), according to the expressions:

$$z(t) = \text{ifft } [B(i) \otimes \text{fft}(t)] = x(t) + jh(t)$$

Where:
ifft denotes an Inverse Fourier Transform,
B(i)=2 for i=[0, N/(2−1)],
B(i)=0 for i=[N/2, N−1],
i denotes an element of an fft(t) array of N elements,
$\otimes$ denotes conjugate,
fft denotes Fast Fourier Transform,
j denotes an imaginary part, and
h(t) denotes a Hilbert transform of an array x(t).

This can be done by using off-the-shelf Hilbert Transform and IFFT programs run on a PC. As evident from the expression above, the Hilbert Transform involves zeroing the coefficient values in all the negative frequency bins of the fft(t) arrays (i.e., array elements 514–1025, inclusive) and doubling the coefficient values in all the positive frequency bins of the fft(t) arrays (i.e., elements 1–513, inclusive). The result is subjected to IFFT, converting each fft(t) array (that has been Hilbert-transformed) into a 1024-element complex array z(t) in which: (1) the real portion contains the original data x(t) enhanced by the windowing and filtering described above, and (2) the imaginary portion contains the Hilbert transform of the same original data.

11. Find an instantaneous phase angle p(t) for each sample position of x(t) in accordance with:

$$p(t) = a\tan\,[h(t)]/[x(t)] = \tan^{-1}[h(t)]/[x(t)].$$

This can be done by programming a PC to carry out the division and the trigonometric calculation set forth immediately above for each of the time samples (t). The result is a phase angle value p(t) for each instant (t) at which the composite FM signals was sampled to generate to arrays x(t);

12. Find the instantaneous frequency f(t) for each sample position of x(t) in accordance with:

$$f(t) = [\tfrac{1}{2}\pi]\{[dp(t)]/[dt]\} = [\tfrac{1}{2}\pi]\{[\Delta p(t)]/[\Delta t]\},$$

Where Δp(t) is the difference in value between two adjacent samples on the instantaneous phase angle p(t), and Δt is the time spacing between two adjacent samples of x(t).
This can be done by programming a PC to carry out the arithmetic operations set forth immediately above for each pair of adjacent values of p(t) and (t), in effect producing an 1024-element array of instantaneous frequency values f(t) for each array x(t);

13. Convert the instantaneous frequencies f(t) to amplitudes of samples of reconstructed ECG waveform (using 56 sample moving average) to get 14-bit long, averaged, reconstructed ECG samples. This can be done by first discarding the first and last 25% of each array f(t) (because of the large attenuation in these portions of the arrays due to the Hamming Window filtering earlier). Because of the 50% overlap of the x(t) arrays described earlier, the elements discarded from one array f(t) is present in the preceding and succeeding array, so this process still derives an instantaneous frequency f(t) for each instant in which the composite FM signals was sampled. The purpose of using a moving average of 56 samples of f(t) is to reduce the influence of noise or other artifacts. The result is a string of averaged values of frequency at a rate of 142.85714 Hz (i.e., the original sampling rate of 8,000 Hz divided by 56, the number of samples used in averaging). For computational convenience, the resulting values can be multiplied by 5 and converted to integer form, to produce a string of 14-bit values representing the instantaneous frequencies at respective 1/142.85714 time slots in the respective ECG signals;

14. Edge detect for FSK/pacer pulse analysis, and encode result into 2-bit encoder data. This can be done as currently carried out in commercial equipment available, for example, from the assignee hereof. In principle, the process involves detecting high-frequency, high-amplitude edges in the composite FM signal, carrying FSK (frequency shift key)/pacer pulse analysis, and encoding detected FSK/pacer pulse data as successive 2-bit values;

15. Format the resulting data into 16-bit samples at 142.85714 Hz, where the top two bits are FSK/pacer data of which 20 bits are stored across ten 16-bit samples;

16. Display/record the reconstructed ECG and any other relevant data. This can be done using frequency to amplitude conversion techniques as currently used commercially, for example by the assignee hereof, and as described in the patents incorporated by reference herein for single-channel ECG data, adapted to displaying three-channel data in this case.

What is claimed is:

1. A method of remotely monitoring at a central station cardiac conditions existing at a remote station, comprising:

deriving three or more ECG waveforms at a local station and frequency modulating a respective carrier in accordance with each of said waveforms to thereby produce three or more respective FM signals;

combining the FM signals into a composite FM signal containing concurrent information from the three or more ECG waveforms;

transmitting the composite FM signal to a central station;

processing the composite FM signal received at the central station both in the time domain and in the frequency domain to reconstruct the three or more individual ECG waveforms.

2. A method as in claim 1 in which said processing comprises estimating local frequencies at portions of the composite FM signal that are substantially closer to each other than zero crossovers of the composite FM signal.

3. A method as in claim 2 in which said processing comprises estimating local phase differences at portions of the FM signal that are substantially closer than said zero crossovers and using the local phase differences to estimate said local frequencies.

4. A method as in claim 3 in which the estimating of local phase differences comprises combining digital samples of the composite FM signal with a phase shifted version of the digital samples.

5. A method as in claim 4 in which the comparing comprises comparing the samples with a Hilbert-transformed version of the samples.

6. A method as in claim 5 in which the processing comprises digitizing the composite FM signal into digital samples in the time domain, converting the time domain samples into frequency domain samples and filtering and separating the frequency domain samples into groups related to the respective ECG waveforms, and converting a Hilbert-transformed version of the frequency domain samples into the time domain.

7. A method of reconstructing at a central station an ECG waveform derived at a remote station, comprising the steps of:

deriving an ECG waveform at a remote station;

frequency modulating a carrier in accordance with the ECG waveform to generate an FM signal related to the ECG waveform and having zero crossovers;

transmitting the FM signal to a central station;

processing the FM signal at the central station to estimate local frequencies thereof at times occurring substantially more frequently than the zero crossovers of the FM signal; and using the estimated local frequencies to reconstruct the ECG waveform at the central station.

8. A method as in claim 7 in which the local frequencies are estimated at a rate at least equal to the carrier frequency.

9. A method as in claim 7 in which the local frequencies are estimated at least at hundreds of time slots between successive zero crossovers.

10. A method as in claim 7 in which the processing comprises processing a digitized version of the FM signal in both the time domain and the frequency domain.

11. A method as in claim 7 in which said processing comprises comparing a version of the FM signal with a phase shifted version thereof to estimate local phase differences for successive samples of the FM signal, and using the estimated phase differences to reconstruct the FM signal.

12. A method of reconstructing an ECG waveform from an FM signal comprising a carrier that is frequency modulated with the ECG waveform, comprising:

digitizing the FM signal into first time domain digital values representing local amplitudes of the FM signal;

converting the time domain digital values into frequency domain digital values representing content of the FM signal at respective frequencies within a band of interest for said ECG waveform;

generating a phase-shifted version of the frequency domain digital values;

converting the frequency domain digital values and the phase-shifted version thereof to respective second and third time-domain digital values;

using said second and third time domain digital values to calculate local frequencies at locations in said FM signal corresponding to at least twice the carrier frequency; and using said local frequencies to reconstruct said ECG waveform.

13. A method as in claim 12 in which the converting to the frequency domain comprises using an FFT process.

14. A method as in claim 12 in which the generating of a phase-shifted version comprises using a Hilbert transform in digital form.

15. A method as in claim 12 including filtering out frequencies outside said band of interest for the ECG waveform.

16. A method of reconstructing a plurality of ECG waveforms from a composite FM signal formed by combining a plurality of carriers FM encoded with respective ones of the ECG waveforms such that a time slot of the composing signal contains information from each of a plurality the ECG waveforms, said composite waveforms having zero crossovers, comprising the steps of:

digitizing the composite signal;

processing the composite signal in the digital domain to estimate local frequencies thereof at times occurring substantially more frequently that said zero crossovers; and using the estimated local frequencies to reconstruct said ECG waveforms.

17. A method as in claim 16 in which said processing comprises processing the composite signal both in the time domain and in the frequency domain.

18. A method as in claim 17 in which said processing comprises filtering a frequency domain version of the composite signals and separating out portions thereof corresponding to frequency bands of the respective ECG waveforms.

19. A method as in claim 18 in which said processing comprises comparing a version of said composite signal with a phase-shifted version thereof to estimate local phase shifts, and using the estimated local phase shifts in estimating said local frequencies.

20. A method as in claim 19 in which said comparing comprises comparing a version of the composite signal with a Hilbert-transformed version thereof.

* * * * *